United States Patent
de Carvalho et al.

(10) Patent No.: US 8,871,123 B2
(45) Date of Patent: Oct. 28, 2014

(54) METHOD OF MAKING AN ABSORBENT CORE HAVING A PLURALITY OF FIRST REGIONS AND A SECOND REGION SURROUNDING EACH OF THE FIRST REGIONS

(75) Inventors: Antonio Carlos Ribeiro de Carvalho, Taubate (BR); Ivair Luiz Duarte, Jardim Florida-Jacarei (BR); Márcia Helena Teixeira Fajolli, São José dos Campos (BR); Francisco Antonio Rimoli, Vila Lavinea-Mogi das Cruzes (BR); Maria Márcia R. Caldas Salles, São José dos Campos (BR)

(73) Assignee: Johnson & Johnson Ind. E Com. Ltda. (BR)

( * ) Notice: Subject to any disclaimer, the term of this patent is extended or adjusted under 35 U.S.C. 154(b) by 0 days.

(21) Appl. No.: 12/185,934

(22) Filed: Aug. 5, 2008

(65) Prior Publication Data
US 2010/0032858 A1    Feb. 11, 2010

(51) Int. Cl.
    *B29C 55/18*    (2006.01)
    *A61F 13/15*    (2006.01)

(52) U.S. Cl.
    CPC .................... *A61F 13/15658* (2013.01)
    USPC ............ 264/119; 264/297.3; 264/301

(58) Field of Classification Search
    USPC ........................ 264/119, 297.3, 301
    See application file for complete search history.

(56) References Cited

U.S. PATENT DOCUMENTS

| | | | |
|---|---|---|---|
| 3,860,002 A * | 1/1975 | Kolbach | 604/365 |
| 4,027,672 A | 6/1977 | Karami | |
| 4,666,647 A * | 5/1987 | Enloe et al. | 264/121 |
| 4,676,784 A | 6/1987 | Erdman et al. | |
| 5,047,023 A | 9/1991 | Berg | |
| 5,941,862 A | 8/1999 | Haynes et al. | |
| 6,037,518 A | 3/2000 | Guidotti et al. | |
| 6,152,906 A | 11/2000 | Faulks et al. | |
| 6,848,894 B2 | 2/2005 | Baker et al. | |
| 2004/0140048 A1 * | 7/2004 | Lindsay et al. | 156/209 |
| 2005/0109442 A1 | 5/2005 | Neubauer et al. | |
| 2006/0206074 A1 | 9/2006 | Bernal et al. | |

FOREIGN PATENT DOCUMENTS

| | | |
|---|---|---|
| CN | 1470226 | 1/2004 |
| DE | 4324802 A1 | 1/1995 |
| EP | 1371348 A2 | 12/2003 |
| WO | WO 97/19659 A1 | 6/1997 |
| WO | WO 02/068002 A2 | 9/2002 |
| WO | WO 2004/011723 A2 | 2/2004 |
| WO | 2006105305 A1 | 10/2006 |
| WO | WO 2007/008124 A1 | 1/2007 |

* cited by examiner

*Primary Examiner* — James Sanders (57) ABSTRACT

The present invention relates to an absorbent article including a absorbent core having a plurality of first regions and a second region, each one of said first regions being arranged in spaced relationship from each of the other first regions and each of the first regions being entirely surrounded by the second region. The present invention also relates to a method of making such a core structure.

6 Claims, 7 Drawing Sheets

METHOD OF MAKING AN ABSORBENT CORE HAVING A PLURALITY OF FIRST REGIONS AND A SECOND REGION SURROUNDING EACH OF THE FIRST REGIONS

FIELD OF THE INVENTION

The present invention generally relates to sanitary absorbent articles and in particular to feminine sanitary absorbent napkins having enhanced breathability, temperature and humidity control characteristics. The present invention also relates to a method of making an absorbent core for use in such article.

BACKGROUND OF THE INVENTION

Externally worn, sanitary absorbent napkins are one of many kinds of feminine protection devices currently available. Sanitary napkins conventionally have a laminate construction including a body-facing liquid permeable layer, an absorbent core layer or layers, and a liquid impermeable garment facing layer. A problem with conventional napkins, due to the laminate construction thereof, is that such articles are not particularly breathable within the absorbent layers of the article. This lack of "internal breathability" within the article construct can cause comfort problems for the user during use of the article. In particular, the lack of internal breathability in conventional articles may cause the users body temperature to rise in a localized area thereby creating discomfort during use. Further, once the article becomes wet, the lack of internal breathability may prevent the article from dying thereby imparting a wet sensation to the user during use.

The inventors of the present invention have discovered a sanitary napkin construction that overcomes the shortcomings of conventional sanitary napkins described above and more particularly have disclosed herein a napkin construction that provides enhanced breathability, temperature and humidity control characteristics. The inventors of the present invention have also discovered a method of making an absorbent core structure for use in such an article.

SUMMARY OF THE INVENTION

In view of the foregoing the present invention provides a method of making an absorbent core structure for a sanitary article including the steps of providing fibrous pulp, maintaining the fibrous pulp in a chamber, mounting a mold to a rotating forming drum, the mold having a first porous portion and a centrally arranged nonporous portion; rotating the mold on the rotating forming drum until the mold is arranged in communication with the chamber, drawing the fibrous pulp into the mold to thereby form a core having a plurality of first regions and a second region, each one of said first regions being arranged in spaced relationship from each of the other first regions and each of the first regions being entirely surrounded by the second region, expelling the core structure from the mold, and conveying the core structure through a calendar roll to compress the core structure until the plurality of first regions and second region have a uniform thickness.

BRIEF DESCRIPTION OF THE DRAWINGS

Examples of embodiments of the present invention will now be described with reference to the drawings, in which.

Examples of embodiments of the present invention will now be described with reference to the drawings, in which.

DETAILED DESCRIPTION OF THE INVENTION

Figure 1:
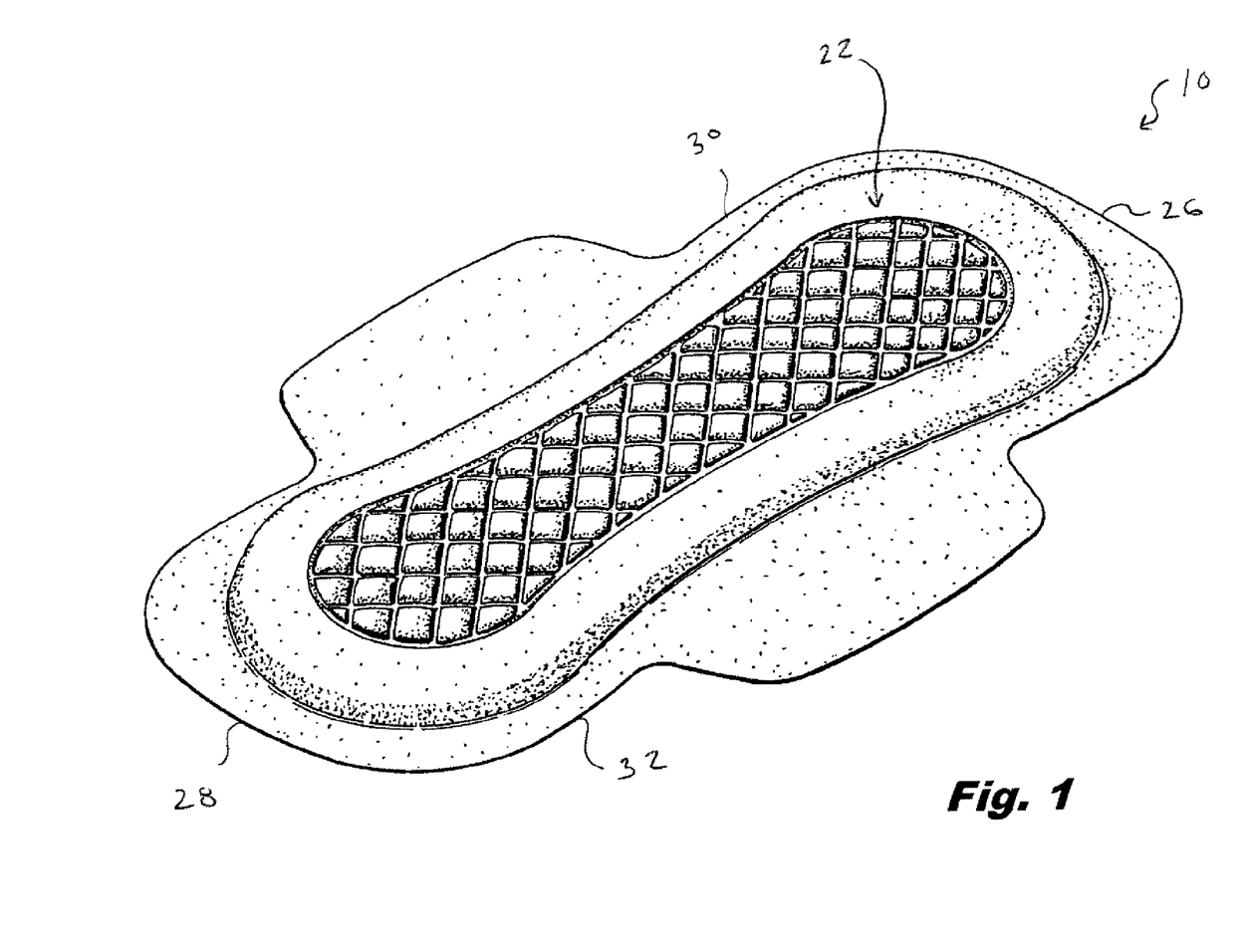
FIG. 1 is a perspective view of a sanitary napkin in accordance with an embodiment of the present invention.
Figure 2:
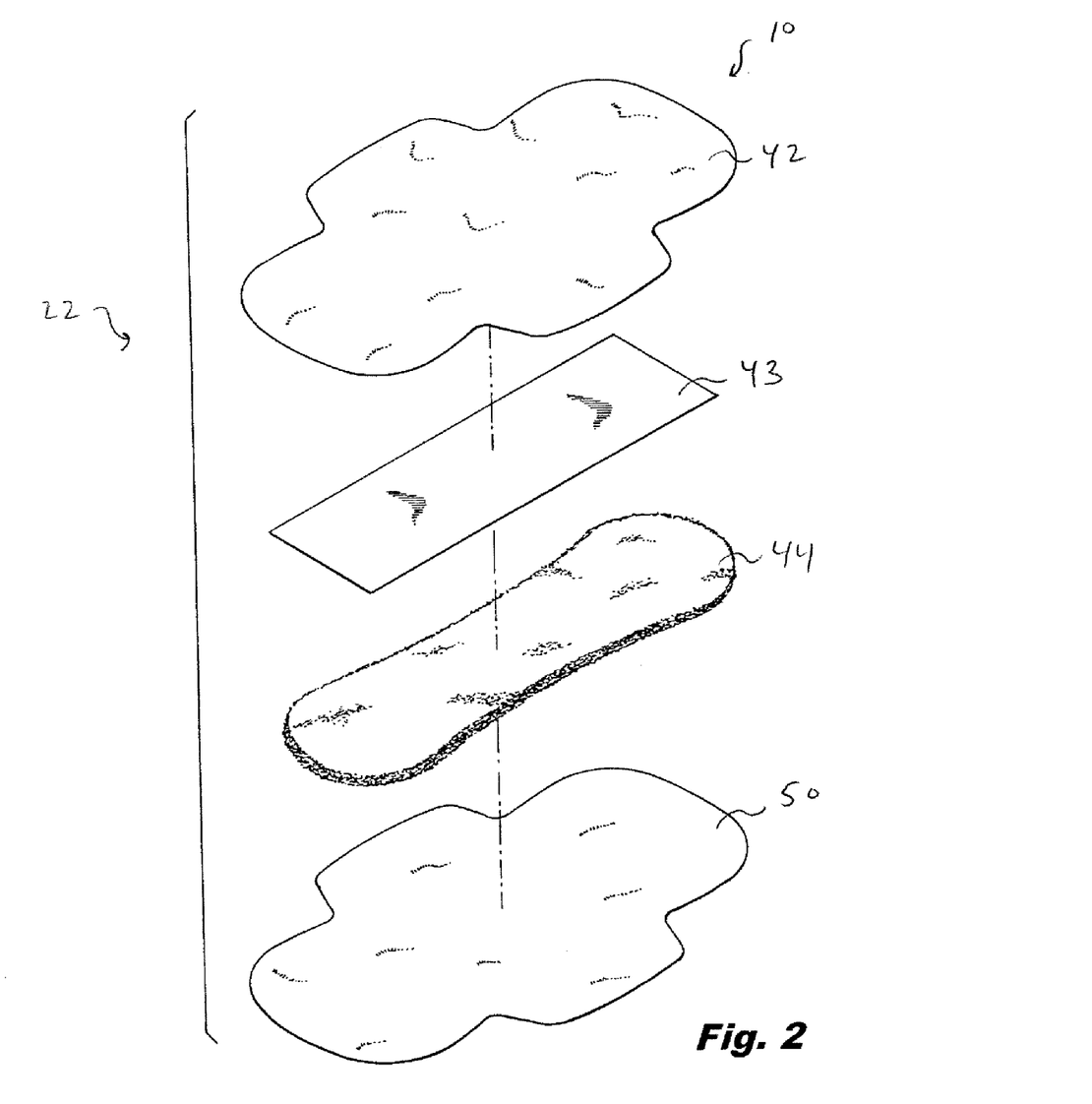
FIG. 2 is an exploded view of the sanitary napkin shown in FIG. 1, according to a first embodiment of the invention, showing the constituent layers thereof.

Referring to FIGS. 1 and 2, there is shown an embodiment of the present invention, a feminine sanitary napkin 10.

The sanitary napkin 10 has a main body 22 with a first transverse side 26 defining a front portion thereof and a second transverse side 28 defining a rear portion thereof. The main body also has two longitudinal sides, namely a longitudinal side 30 and a longitudinal side 32.

As depicted in FIG. 2, the main body 22, according to a first embodiment of the invention, is of a laminate construction and includes a fluid-permeable cover layer 42, a transfer layer 43, an absorbent core 44 and a fluid-impervious barrier layer 50.

Figure 3:
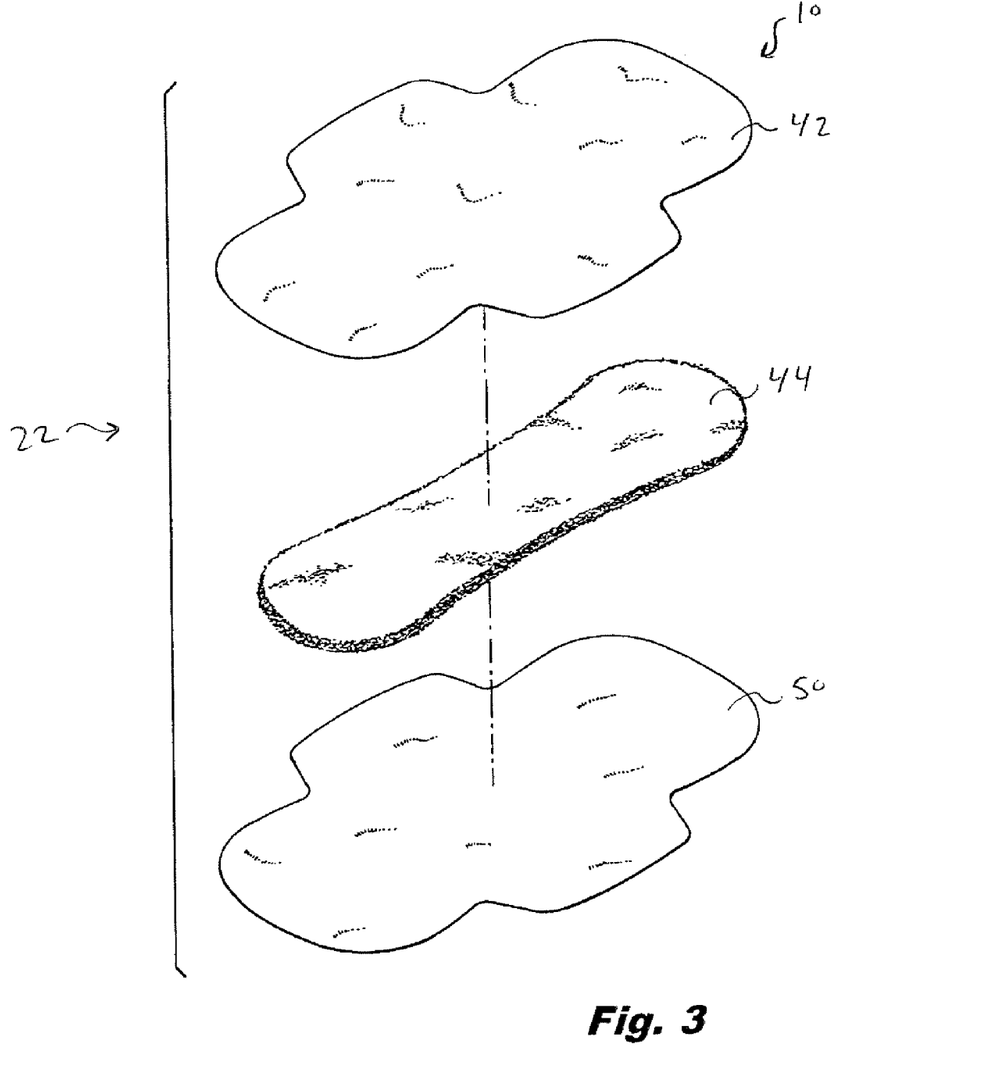
FIG. 3 is an exploded view of the sanitary napkin shown in FIG. 1, according to a second embodiment of the invention, showing the constituent layers thereof.
Figures 4, 5, 6, 7:
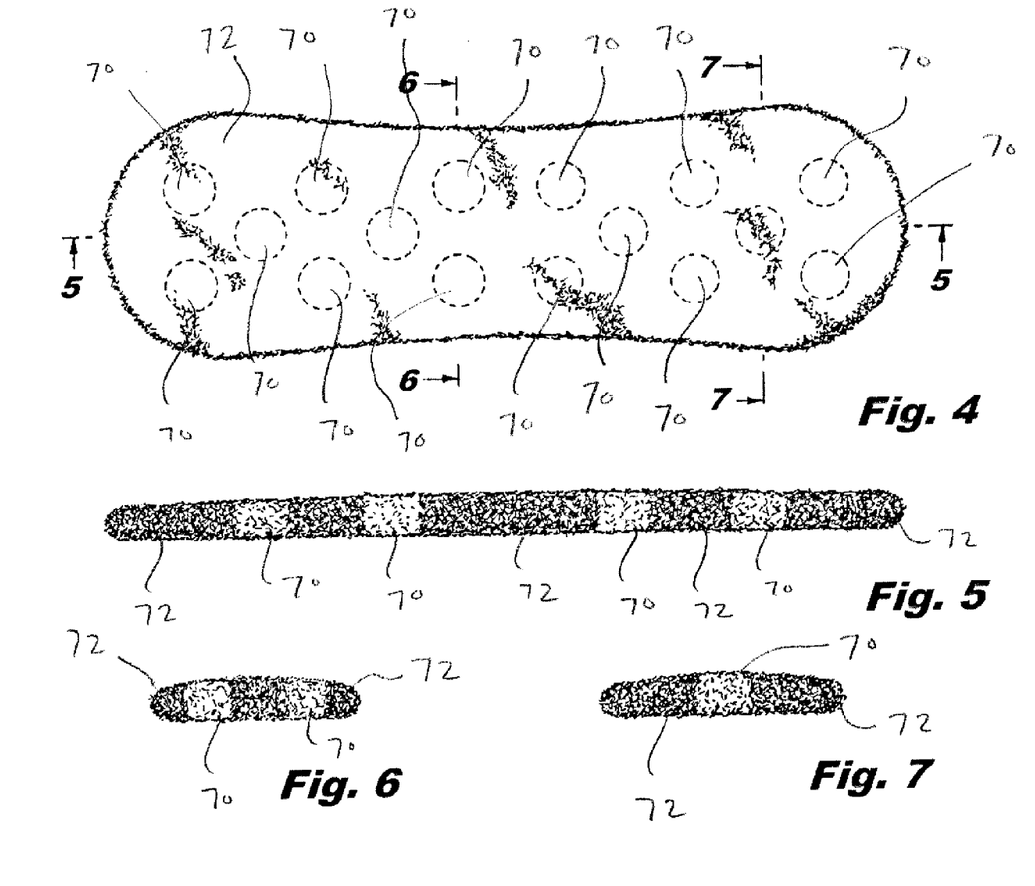
FIG. 4 is a top plan view of the core layer of the sanitary napkin shown in FIG. 1 showing the first and second concentric regions thereof.
FIG. 5 is a sectional view taken along line 5-5 in FIG. 4.
FIG. 6 is a sectional view taken along line 6-6 in FIG. 4.
FIG. 7 is a sectional view taken along line 7-7 in FIG. 4.

As depicted in FIG. 3, the main body 22, according to a second embodiment of the invention, is of a laminate construction and includes a fluid-permeable cover layer 42, an absorbent core 44, and a fluid-impervious barrier layer 50.

Referring to FIGS. 4-7, the absorbent core 44 includes a plurality of first regions 70 and a second region 72. As shown in FIG. 3, each of the plurality of first regions 70 are arranged in spaced relationship to one another and are entirely surrounded by the second region 72.

Each of the plurality of first regions 70 has a basis weight in the range of between 7.5 gsm (g/m$^2$) and 555 gsm and the second region 72 has a basis weight in the range of between 150 gsm and 650 gsm. The basis weight of each of the plurality of first regions 70 is selected such that is less than the basis weight of the second region 72. In particular the basis weight of each of the plurality of first regions 70 is selected such that each region 70 has a basis weight of about 5% to about 85% the basis weight of the second region 72. In one preferred embodiment of the invention the basis weight of each of the plurality of first regions 70 is selected such that each region 70 has a basis weight of about 50% the basis weight of the second region 72.

Each of the plurality of first regions 70 has a density that is less than the density of the second region. Specifically each of the first regions 70 preferably has a density in the range from about 0.017 g/cm$^3$ to 0.200 g/cm$^3$ and the second region 72 has a density in the range of about 0.035 g/cm$^3$ to 0.400 g/cm$^3$. In one preferred embodiment of the invention each of the first regions 70 has a density that is less than 80% the density of the second region 72, and more preferably less than 50%.

While in one preferred embodiment of the invention each of the first regions 70 have the same density, it is possible that individual first regions 70 have a different densities from one another provided that each of the first regions 70 has a density less than the density of the second region 72.

Preferably the plurality of first regions 70 (i.e. the summation of the area over which the first regions extend) extend over about 5% to about 30% the surface area of the core 44 and the second region 72 extends over about 70% to 95% of the core. The absorbent core 44, including those areas defined by the plurality of first regions 70 and the second region 72, preferably has a uniform thickness between about 0.5 mm and about 12 mm. In a preferred embodiment of the invention, the absorbent core 44 comprises between about 75% to 100% cellulose fibers by weight and 0% to 25% superabsorbent polymer by weight. In a particularly preferred embodiment, the plurality of first regions 70 and the second region have 72 the same identical material composition. Also, preferably, the plurality of first regions 70 and second region 72 are composed of a single layer of material, that is the plurality of first regions 70 and second region 72 are not formed by layering two distinct layers one on top of another.

Main Body—Cover Layer

The cover layer 42 may be a relatively low density, bulky, high-loft non-woven web material. The cover layer 42 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 42 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transports it away from the body and the point of deposition. Therefore, the cover layer contributes little to the time taken for the napkin to absorb a given quantity of liquid (penetration time).

Advantageously, the fibers that make up the cover layer 42 should not lose there physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the underlying layers of the absorbent article. Thus, the cover layer 42 is advantageously wettable, hydrophilic and porous. When composed of synthetic hydrophobic fibers such as polyester or bi-component fibers, the cover layer 42 may be treated with a surfactant to impart the desired degree of wettability.

In one preferred embodiment of the present invention the cover is made from a 16 gsm thermal bonded polypropylene fiber nonwoven of the type commercially available from Polystar Company, Salvador, BA, Brazil under product code 142250.

Alternatively, the cover layer 42 can also be made of polymer film having large pores. Because of such high porosity, the film accomplishes the function of quickly transferring body fluid to the underlying layers of the absorbent article. A suitable cover material of this type is commercially found on the STAYFREE Dry Max Ultrathin product distributed by McNeil-PPC, Inc.

The cover layer 42 may be embossed to the remainder of the absorbent core 44 in order to aid in promoting hydrophilicity by fusing the cover to the next layer. Such fusion may be effected locally, at a plurality of sites or over the entire contact surface of cover layer 42 and absorbent core 44. Alternatively, the cover layer 42 may be attached to the absorbent core 44 by other means such as by adhesion.

Main Body—Transfer Layer

Adjacent to the cover layer 42 on its inner side and bonded to the cover layer 42 is the transfer layer 43. The transfer layer 43 provides the means of receiving body fluid from the cover layer 42 and holding it until the underlying absorbent core 44 has an opportunity to absorb the fluid, and therefore acts as a fluid transfer or acquisition layer. The transfer layer 43 is, preferably, more dense than and has a larger proportion of smaller pores than the cover layer 42. These attributes allow the transfer layer 43 to contain body fluid and hold it away from the outer side of the cover layer 42, thereby preventing the fluid from rewetting the cover layer 42 and its surface. However, the transfer layer is, preferably, not so dense as to prevent the passage of the fluid through the layer 43 into the underlying absorbent core 44.

The transfer layer 43 be composed of fibrous materials, such as wood pulp, polyester, rayon, flexible foam, or the like, or combinations thereof. The transfer layer 43 may also comprise thermoplastic fibers for the purpose of stabilizing the layer and maintaining its structural integrity. The transfer layer 43 may be treated with surfactant on one or both sides in order to increase its wettability, although generally the transfer layer 43 is relatively hydrophilic and may not require treatment. The transfer layer 43 is preferably bonded or adhered on both sides to the adjacent layers, i.e. the cover layer 42 and the underlying absorbent core 44.

Examples of suitable materials for the transfer layer are through air bonded pulp sold by Buckeye of Memphis, Tenn., under the designation VIZORB 3008, which has a basis weight of 110 gsm, VIZORB 3042, which has a basis weight of 100 gsm, VIZORB 3010, which has a basis weight of 90 gsm and others.

Main Body—Absorbent Core

In one preferred embodiment of the invention, the absorbent core 44 is a blend or mixture of cellulosic fibers and superabsorbent disposed therein. Cellulosic fibers that can be used in the absorbent core 44 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. The flexibility of the material may also be improved by mechanically working the material or tenderizing the material.

The absorbent core 44 can contain any superabsorbent polymer (SAP), which are well known in the art. For the purposes of the present invention, the term "superabsorbent polymer" (or "SAP") refers to materials, which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc.

In one preferred embodiment of the invention the absorbent core 44 includes between 50% and 100% cellulose pulp by weight and 0% and 50% superabsorbent polymer by weight.

In one specific example of the invention, the absorbent core 44 is constructed from about 93% fluff pulp by weight, suitable pulp commercially available as Golden Isles Fluff Pulp 420#HD 7% Moisture, from GP Cellulose, Brunswick, Ga., USA, mixed with about 7% superabsorbent polymer by weight, suitable SAP commercially available as Aqua Keep SA70N from Sumitomo Seika Chemicals Co., Ltd., Osaka, Japan.

Method of Making the Absorbent Core

A description of the method of making the absorbent core according to the present invention will now be provided with reference to FIGS. 8-12 which depicts an apparatus 200 for making the absorbent core structure according to the present invention. The pulp used to form the absorbent core 44 is a bleached softwood pulp, produced by a Kraft process. The pulp is provided by the manufacturer as a pulp board 202 in rolled form, the roll identified by the reference numeral 204 in FIG. 8. The pulp board 202 is conveyed from the roll 204 to a device 206 for grinding the pulp board 202 into fibrous pulp 205. The fibrous pulp 205 is released from the grinding device 206 into a chamber 208 for holding the fibrous pulp 205. The apparatus 200 may further optionally include a device 207 for introducing superabsorbent polymer into the chamber 208 to thereby form a fibrous pulp and superabsorbent mixture. Any conventional device suitable for this purpose, and known to those of skill in the art, may be used for introducing the superabsorbent into the chamber 208.

Figure 8:
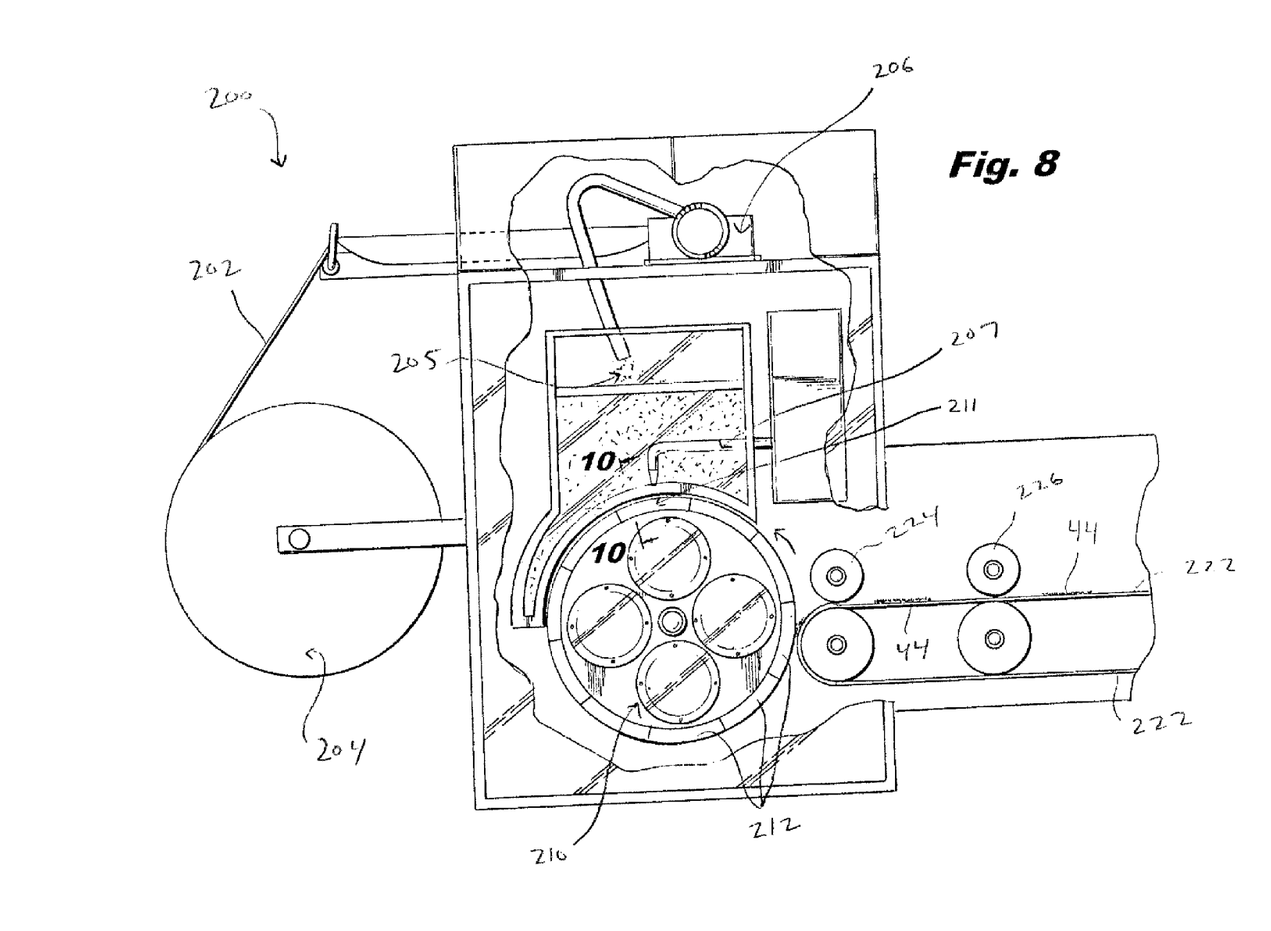
FIG. 8 is a schematic view showing an apparatus for making the core layer shown in FIGS. 3-7.
Figure 9:
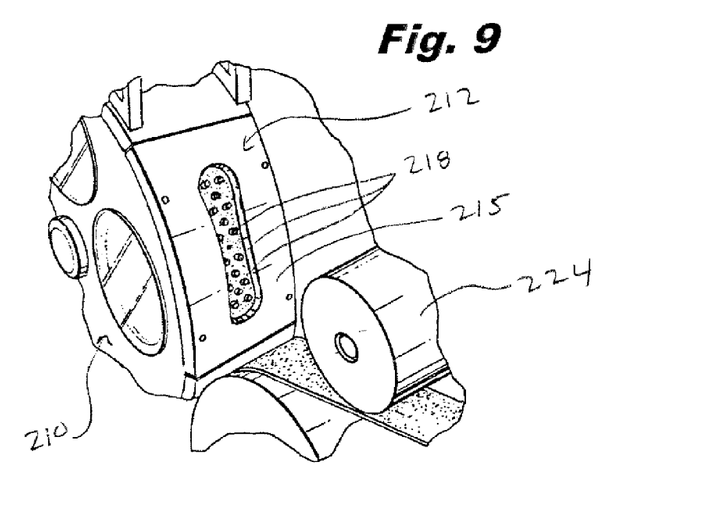
FIG. 9 is a detailed perspective view of a portion of the apparatus shown in FIG. 8.
Figure 10:
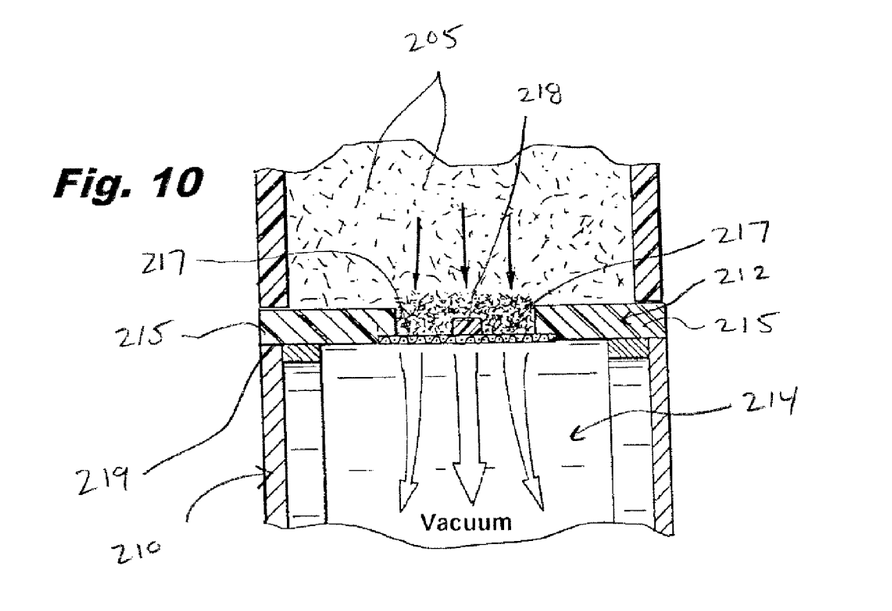
FIG. 10 is a sectional view of the apparatus shown in FIG. 8 taken along line 10-10 thereof.

The chamber 208 has a partially open bottom portion 211 that communicates with a rotating forming drum 210. The rotating forming drum 210 has a plurality of molds 212 mounted thereto. As the forming drum 210 rotates, each of the molds 212 are sequentially arranged in communication with the open portion 211 of the chamber 208 to thereby receive fibrous pulp 205 from the chamber 208. In FIG. 8, the forming drum 210 rotates in a counterclockwise manner during operation of the apparatus 200. As shown in FIG. 10, the forming drum 210 includes a portion 214 that is under vacuum. As shown in FIGS. 9 and 10, the mold 212 includes a porous screen 217 structure in the shape of the second region 72 of the core 44. As the mold 212 passes over portion 214 of the forming drum 210 the vacuum functions to draw the fibrous pulp 205 from the chamber 208 into the mold 212 by drawing air through the porous screen 217 of the mold 212.

As shown in detail in FIG. 10, the mold 212 includes a nonporous mounting plate portion 215 that surrounds the porous screen 217 portion of the mold 212. As best seen in FIG. 10, the mounting plate portion 215 of the mold 212 is mounted to the periphery 219 of the forming drum 210, thereby enabling each of the molds 212 to rotate with the rotating forming drum 210. The porous screen 217 portion of the mold 212 is arranged in the shape of the second region 72 of the core 44. The mold 212 further includes a plurality of nonporous projections 218, each projection 218 being in the shape of one of the plurality of first regions 70. Each of nonporous projections 218 has a height that is less than the height of the mounting plate portion 215. The structure of the mold 212 described above, during use, causes a greater amount of fibrous pulp 205 to be drawn into the porous screen 217 portion of the mold 212 relative to the amount of fibrous pulp 205 drawn into each nonporous projections 218.

Figure 11:
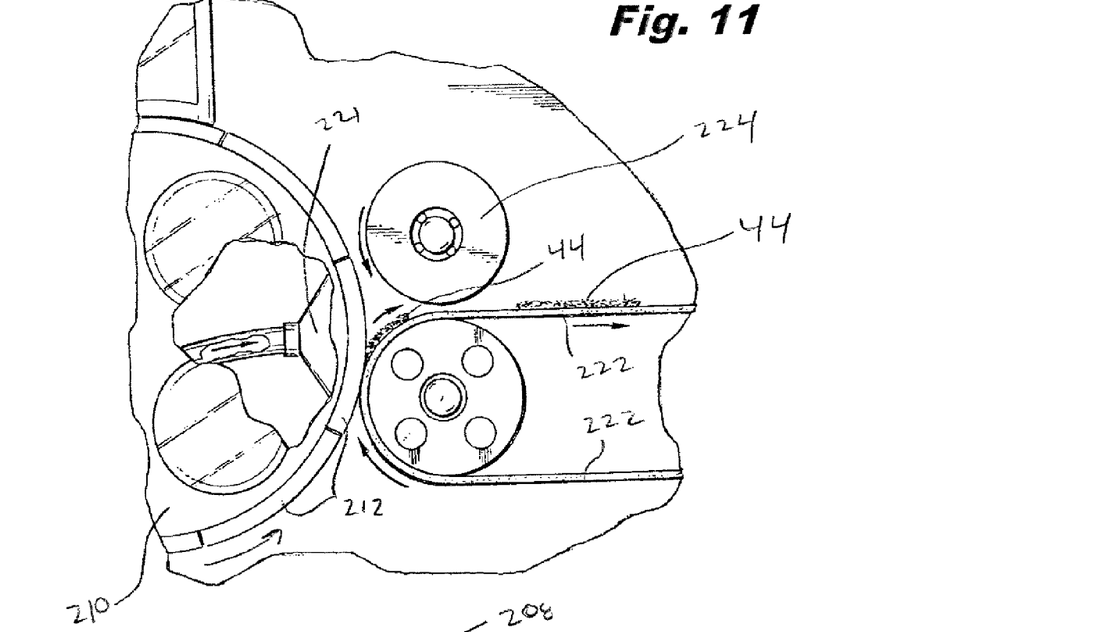
FIG. 11 is a detailed elevation view of a portion of the apparatus shown in FIG. 8.
Figure 12:
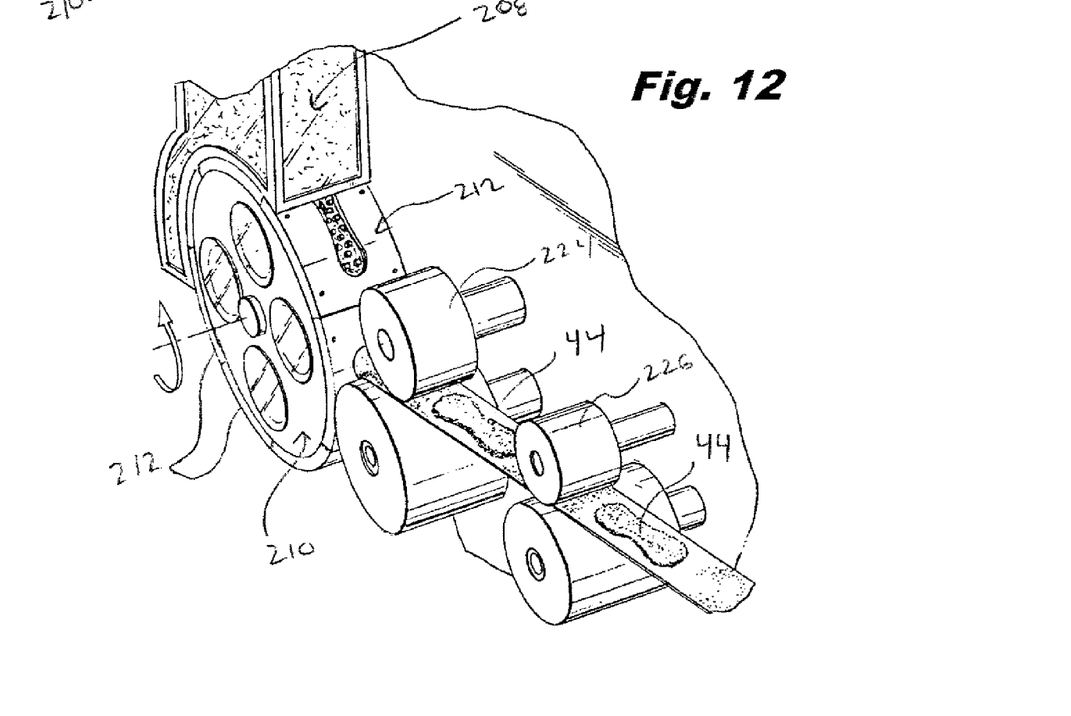
FIG. 12 is a detailed perspective view of a portion of the apparatus shown in FIG. 8.

After the mold 212 is rotated under the partially open bottom portion 211 of the chamber 208, the mold 212 is further rotated by the rotating forming drum 210. As shown in FIG. 11, the rotating forming drum 210 includes a portion 221 that expels air outwardly from within the drum 210. The portion 221 of the drum 210 functions to expel the core 44 structure formed within the mold 212 onto a belt 222. The belt 222 functions to convey the core 44 to a first calendar roll 224. The calendar roll 224 functions to reduce the thickness of the core 44 so that the first 70 and second 72 regions of the core 44 have a uniform thickness but have different basis weights. As shown in FIG. 12, the core 44 may optionally be further conveyed by the belt 222 to a second calendar roll 226 that functions to further reduce the thickness of the core 44.

Main Body-Barrier Layer

Underlying the absorbent core 44 is a barrier layer 50 comprising liquid-impervious film material so as to prevent liquid that is entrapped in the absorbent core 44 from egressing the sanitary napkin and staining the wearer's undergarment. The barrier layer 50 is preferably made of polymeric film, although it may be made of liquid impervious, air-permeable material such as repellent-treated non-woven or micropore films or foams.

The barrier layer may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 42 and the barrier layer 50 are joined along their marginal portions so as to form an enclosure or flange seal that maintains the absorbent core 44 captive. The joint may be made by means of adhesives, heat-bonding, ultrasonic bonding, radio frequency sealing, mechanical crimping, and the like and combinations thereof.

Positioning adhesive may be applied to a garment facing side of the barrier layer for securing the napkin 10 to the garment during use. The positioning adhesive may be covered with removable release paper so that the positioning adhesive is covered by the removable release paper prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

The absorbent article of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof, hot melt adhesives based on suitable block copoylmers—suitable block copolymers for use in the invention include linear or radial co-polymer structures having the formula (A–B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Where adhesive is used, a release strip may be applied to protect the adhesive on the absorbent article prior to attaching the absorbent article to the crotch. The release strip can be formed from any suitable sheet-like material adheres with sufficient tenacity to the adhesive to remain in place prior to use but which can be readily removed when the absorbent article is to be used. Optionally, a coating may be applied to release strip to improve the ease of removabilty of the release strip from the adhesive. Any coating capable of achieving this result may be used, e.g., silicone.

Any or all of the cover, absorbent layer, transfer layer, backsheet layer, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The absorbent article may include other known materials, layers, and additives, such as, foam, net-like materials, perfumes, medicaments or pharmaceutical agents, moisturizers, odor control agents, and the like. The absorbent article can optionally be embossed with decorative designs.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated by the present invention are asymmetrical and symmetrical absorbent articles having parallel longitudinal edges, dog bone- or peanut-shaped, as well as articles having a tapered construction for use with thong-style undergarments. From the foregoing description, one skilled in the art can ascertain the essential characteristics of this invention, and without departing from the spirit and scope thereof, can make various changes and modifications. Embodiments set forth by way of illustration are not intended as limitations on the variations possible in practicing the present invention.

EXAMPLE

Specific inventive examples of the present invention are described below.

Inventive Example #1

An example of an sanitary napkin according to the invention was constructed as follows. The body facing cover layer was constructed from a 16 gsm thermal bonded nonwoven material constructed from 100% hydrophilic polypropylene fibers, commercially available form Polystar Company, Salvador, Brazil under product code 142250. An absorbent core was arranged below the cover and was formed by the process described herein with reference to FIGS. 8-1. The absorbent core has a plurality of first regions extending over a surface area of 1256.6 mm$^2$ (i.e. the summation of the area over which the first regions extend) and second region with a surface area of 10548.7 mm$^2$. Each of the plurality of first regions had a basis weight of 212 g/m$^2$ and the second region had a basis weight of 424 g/m$^2$. Each of the plurality of first regions 70 had a density of 0.035 g/cm$^3$ and the second region 72 had a density of 0.071 g/cm$^3$. The absorbent core had a composition of about 93% by weight of pulp and about 7% by weight of superabsorbent polymer. The pulp was Golden Isles Fluff Pulp 420#HD 7% Moisture, commercially available from GP Cellulose, Brunswick, Ga., USA. The superabsorbent polymer was Aqua Keep SA70N commercially available from Sumitomo Seika Chemicals Co., Ltd., Osaka, Japan. A barrier layer was arranged below the core and was formed from a 24 gsm polyethylene film commercially available from Clopay do Brasil, Jundiaí, Brazil, under product code 113689.

Applications of the absorbent article according to the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. A method of making an absorbent core structure for a sanitary article comprising the steps of:
   providing fibrous pulp;
   maintaining the fibrous pulp in a chamber;
   mounting a mold to a rotating forming drum, the mold having:
   i) a first porous portion;
   ii) a nonporous mounting plate portion surrounding the first porous portion, the nonporous mounting plate having a height; and
   iii) a plurality of nonporous projections, the plurality of nonporous projections having a height that is less than the height of the mounting plate portion for receiving less fibrous pulp than the first porous portion;
   rotating the mold on the rotating forming drum until the mold is arranged in communication with the chamber;
   drawing the fibrous pulp into the mold to thereby form a core having a plurality of first regions and a second region, each one of said first regions being arranged in spaced relationship from each of the other first regions and each of the first regions being entirely surrounded by the second region, the mold being adapted so that each of the plurality of first regions has a basis weight and the second region has a basis weight that is different than the basis weight of each of the first regions; and each of the plurality of nonporous projections being in the shape of one of the plurality of first regions;
   expelling the core structure from the mold; and
   conveying the core structure through a calendar roll to compress the core structure until the plurality of first regions and second region have a uniform thickness to thereby provide a core structure wherein the plurality of first regions and second region have different basis weights but a uniform thickness.

2. The method according to claim 1, wherein the fibrous pulp is drawn into the mold by means of a vacuum arranged internally within the rotating forming drum.

3. The method according to claim 2, wherein the core structure is expelled from the mold by means of an airflow that is expelled outwardly from within the forming drum.

4. The method according to claim 3, wherein the step of conveying the core structure through a calendar roll, comprises the steps of conveying the core structure through a first calendar roll.

5. The method according to claim 4, further comprising the steps of:
   providing pulp board in the form of a roll;
   conveying the pulp board to a device for grinding the pulp board into fibrous pulp;
   arranging the fibrous pulp in the chamber.

6. The method according to claim 5, further comprising the step of:
   introducing superabsorbent polymer into the chamber.

* * * * *